US00PP28626P2

(12) United States Plant Patent
Zaiger et al.

(10) Patent No.: US PP28,626 P2
(45) Date of Patent: Nov. 14, 2017

(54) APRICOT TREE NAMED 'BALBOA'

(50) Latin Name: *Prunus armeniaca*
Varietal Denomination: Balboa

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 59 days.

(21) Appl. No.: 14/999,263

(22) Filed: Apr. 18, 2016

(51) Int. Cl.
*A01H 5/08* (2006.01)

(52) U.S. Cl.
USPC ..... Plt./186

(58) Field of Classification Search
USPC ..... Plt./156, 180, 186
See application file for complete search history.

*Primary Examiner* — Susan McCormick Ewoldt
*Assistant Examiner* — Karen Redden

(57) ABSTRACT

A new and distinct variety of apricot tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree having a vigorous, semi-spreading growth habit.
2. Tree being a regular and productive bearer of medium to large size fruit.
3. Fruit with an attractive orange skin color.
4. Fruit with good flavor and eating quality.
5. Fruit with good handling and shipping quality.

1 Drawing Sheet

Botanical designation: *Prunus armeniaca.*
Variety denomination: 'Balboa'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecitics are exemplary. It was against this background of our activities that the present variety of interspecific tree was originated and asexually reproduced by us in our experimental orchard located near Modesto, Stanislaus County, Calif.

Prior Varieties

Among the existing varieties of apricot trees, which are known to us, and mentioned herein 'Brittney Gold' Apricot (U.S. Plant Pat. No. 13,504), 'Moniqui' Apricot (non-patented) and the proprietary non-patented apricot seedlings '376LH543' and '337LC174'.

STATEMENT REGARDING FEDERALLY SPONSORED RESEARCH AND DEVELOPMENT

Not applicable.

ORIGIN OF THE VARIETY

The new and distinct variety of apricot tree (*Prunus armeniaca*) was originated by us in our experimental orchard located near Modesto, Calif. from an open pollinated non-patented apricot seedling selection with the field identification number '376LH543'. The seed parent (376LH543) originated as a cross between the proprietary non-patented apricot seedling selection '337LC174' and 'Moniqui' Apricot (non-patented). A large number of these open pollinated seedlings were planted and maintained on their own root system and under close and careful observation we recognized the desirable tree and fruit characteristics of the present seedling and selected it in 2001 for additional asexual propagation and commercialization.

ASEXUAL REPRODUCTION OF THE VARIETY

In 2001 asexual reproduction of the new and distinct variety of apricot tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new and distinct variety of apricot tree (*Prunus armeniaca*) is of large size, vigorous, semi-spreading growth and a regular and productive bearer of medium to large size, orange flesh, freestone fruit with good flavor and eating quality. The fruit is further characterized by having an attractive orange skin color with good handling and storage quality. In comparison to its non-patented proprietary apricot seed parent '376LH543' the fruit of the new variety is approximately 33 days later in maturity. In comparison to the commercial variety 'Brittney Gold' Apricot (U.S. Plant Pat. No. 13,504) the fruit of the new variety is larger in size and is approximately 19 days later in maturity.

DESCRIPTION OF THE PHOTOGRAPH

The accompanying color photographic illustration shows typical specimens of the foliage and fruit of the present new apricot variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 13 year old tree and the colors are as nearly true as is reasonably possible in a color representation of this type.

DESCRIPTION OF THE VARIETY

The following is a detailed botanical description of the new variety of apricot tree, its flowers, foliage and fruit, as based on observations of 13 year old specimens grown near Modesto, Calif., with color in accordance with Munsell Book of Color published in 1958.

Tree:

*Size*.—Large, usually pruned to 3 to 3.5 meters in height and width for economical harvesting of fruit. Varies with different cultural practices.

*Vigor*.—Vigorous, tree growth of approximately 1.5 to 2 meters the first growing season. Varies slightly with cultural practices, type and fertility of soil and climatic conditions.

*Form*.—Semi-spreading, usually pruned to vase shape.

*Branching habit*.—Semi-spreading, crotch angle approximately 35°, increases with heavy crop load.

*Productivity*.—Productive, thinning and spacing of fruit necessary for desired market size. Fruit set varies with climatic conditions during bloom time.

*Bearer*.—Regular, adequate fruit set 11 consecutive years. No alternate bearing observed.

*Fertility*.—Self fertile, sets fruit under bag.

*Density*.—Medium dense, usually pruned to vase shape to increase air movement and sunlight to center of tree to enhance fruit color and health of fruit spurs.

*Hardiness*.—Hardy in all stone fruit growing areas of California. Tree grown in USDA Hardiness Zone 9. Winter chilling requirement approximately 800 hours at or below 45°.

Trunk:

*Size*.—Medium. Average circumference 66.0 cm at 25.4 cm above ground on a 13 year old tree.

*Stocky*.—Medium stocky.

*Texture*.—Medium shaggy, roughness increases with age.

*Color*.—Varies from 2.5Y 6/2 to 2.5Y 5/2.

Branches:

*Size*.—Medium. Average circumference 16.8 cm at 1.2 meters above ground. Crotch angle approximately 35°, increases with heavy crop load.

*Surface texture*.—New growth relatively smooth. Mature growth medium rough, roughness increases with age.

*Lenticels*.—Average number 22 in a 25.8 square cm area. Average length 3.6 mm. Average width 2.1 mm. Color varies from 10YR 6/10 to 10YR 6/12.

*Color*.—New growth varies from 5GY 6/8 to 7.5R 2/8. Mature growth varies from 7.5YR 3/4 to 7.5YR 2/4, varies with age of growth.

Leaves:

*Size*.—Medium to large. Average length 79.6 mm. Average width 73.4 mm.

*Form*.—Ovate.

*Apex*.—Acuminate.

*Base*.—Cuneate.

*Margin*.—Doubly serrate.

*Thickness*.—Medium.

*Surface texture*.—Upper surface relatively smooth, slight indentations over midrib and leaf veins. Lower surface relatively smooth, except for small ridges created by midrib and pinnate venation. Both upper and lower surfaces glabrous.

*Petiole*.—Large. Average length 31.7 mm. Average width 1.5 mm. Longitudinally grooved. Surface — glabrous. Color varies from 2.5GY 6/6 to 7.5R 2/8.

*Glands*.—Type — globose. Size — medium to large. Average length 1.0 mm. Average diameter 0.8 mm. Average number 4, varies from 3 to 5. Located primarily on the upper portion of petiole and base of leaf blade. Color varies from 2.5GY 6/6 to 7.5R 2/8.

*Stipules*.—Average number 2. Average length 7.3 mm. Edges — pectinate. Color varies from 5GY 7/6 to 2.5R 4/10.

*Color*.—Upper surface varies from 5GY 3/6 to 5GY 4/4. Lower surface varies from 2.5GY 5/4 to 2.5GY 4/4. Midvein color varies from 7.5Y 7/6 to 7.5Y 6/6.

Flower buds:

*Size*.—Medium to large. Average length 13.8 mm. Average diameter 9.5 mm. Hardiness: Hardy with respect to California winters.

*Density*.—Medium dense.

*Form*.—Conical, becoming elongated just before opening.

*Pedicel*.—Average length 3.2 mm. Average width 1.2 mm. Surface — glabrous. Color varies from 2.5GY 7/6 to 5GY 7/6.

*Color*.—Varies from 7.5RP 8/6 to 7.5RP 7/8.

*Number of buds per spur*.—Average number 13, varies from 11 to 15.

Flowers:

*Blooming period*.—Date of First Bloom Feb. 24, 2015. Date of Petal Fall Mar. 5, 2015, varies slightly with climatic conditions.

*Size*.—Large. Average height 17.9 mm. Average diameter 32.4 mm.

*Petals*.—Normally 5, alternately arranged to sepals. Petal apex — rounded. Petal base — truncate. Size — medium to large. Average length 14.8 mm. Average width 15.9 mm. Form — orbicular. Margin — sinuate. Arrangement — overlapping. Color varies from 7.5RP 9/2 to 7.5RP 8/4, fades with age of flower. Both upper and lower surfaces glabrous.

*Sepals*.—Normally 5, alternately arranged to petals. Size — large. Average length 6.3 mm. Average width 6.2 mm. Shape — ovate. Apex — rounded to triangular. Both upper and lower surfaces glabrous. Margin — entire. Color — upper surface varies from 2.5R 4/6 to 2.5R 3/8. Lower surface varies from 2.5R 3/8 to 2.5R 2/6.

*Stamens*.—Average number per flower 32. Average filament length 12.1 mm. On average, the stamens are above the height of the petals. Filament color varies from N 9.5/(white) to 7.5RP 8/4. Anther color varies from 5Y 8/8 to 58/10.

*Pollen*.—Present, self fertile, sets fruit under bag. Color varies from 2.5Y 7/12 to 5Y 7/12.

*Pistil*.—Number — normally 1. Average length 17.8 mm. Surface — pubescent. Position of stigma an average of 1.6 mm above anthers. Color varies from 10Y 8.5/4 to 2.5GY 8/4.

*Fragrance*.—Moderate aroma.

*Color*.—Varies from 5RP 8/4 to 5RP 9/2.

*Pedicel*.—Average length 3.8 mm. Average width 1.3 mm. Surface — glabrous. Color varies from 2.5GY 6/6 to 5GY 7/6.

*Number flowers per flower bud*.—Average 2, varies from 1 to 2.

Fruit:

*Maturity when described*.—Firm ripe and ready for consumption.

*Date of first picking*.—Jul. 29, 2015.

*Date of last picking*.—Aug. 8, 2015, varies slightly with climatic conditions.

*Size*.—Medium to large. Average diameter axially 56.3 mm. Average transversely in suture plane 58.9 mm. Average across suture plane 55.0 mm. Average weight 110.8 grams, varies slightly with fertility of the soil, amount of thinning and climatic conditions.

*Form*.—Globose.

*Suture*.—Slightly lipped.

*Vential surface*.—Slightly lipped.

*Apex*.—Slightly retuse.

*Base*.—Flat.

*Stem cavity*.—Rounded to slightly elongated in suture plane. Average depth 4.0 mm. Average diameter 4.5 mm.

Stem:

*Size*.—Small. Average length 7.2 mm. Average diameter 2.6 mm.

*Color*.—Varies from 5GY 5/8 to 5GY 4/6.

Flesh:

*Ripens*.—Evenly.

*Texture*.—Firm, meaty.

*Fibers*.—Few, small, tender.

*Firmness*.—Good, comparable to other commercial apricot varieties.

*Aroma*.—Slight.

*Amydgalin*.—Undetected.

*Eating quality*.—Good.

*Flavor*.—Good, with a good balance between acid and sugar.

*Juice*.—Moderate amount, enhances flavor.

*Acidity*.—Not available.

*Brix*.—Average Brix 18.3°, varies slightly with amount of fruit per tree and climatic conditions.

*Color*.—Varies from 10YR 7/10 to 8.75YR 7/12.

*Pit cavity*.—Average length 30.4 mm. Average width 25.9 mm. Average depth 8.5 mm. Color 6.25YR 6/12.

Skin:

*Thickness*.—Medium.

*Surface*.—Smooth.

*Pubescence*.—Slight amount, short in length.

*Tendency to crack*.—None.

*Color*.—Varies from 7.5YR 7/10 to 8.75YR 7/12.

*Tenacity*.—Tenacious to flesh.

*Astringency*.—Undetected.

Stone:

*Type*.—Freestone, weak adherence to flesh.

*Size*.—Medium. Average length 28.4 mm. Average width 22.9 mm. Average thickness 13.1 mm.

*Form*.—Ovoid.

*Base*.—Flat.

*Apex*.—Rounded.

*Surface*.—Lightly pitted throughout. One shallow groove on each side of suture extending from base toward apex.

*Sides*.—Unequal, one side extending further outward from suture plane.

*Ridges*.—Very small and short, extending from base towards apex.

*Tendency to split*.—None.

*Color*.—Varies from 10YR 4/2 to 2.5Y 3/4 when dry.

Kernel:

*Size*.—Medium to large. Average length 20.8 mm. Average width 14.8 mm. Average thickness 8.5 mm.

*Form*.—Ovate.

*Viability*.—Viable, complete embryo development.

*Skin color*.—Varies from 7.5YR 4/6 to 7.5YR 3/6.

Use: Dessert.

*Market*.—Local and long distance.

Keeping quality: Good, held firm in cold storage for 3 weeks at 38° to 42° F. without shriveling, internal breakdown of flesh or appreciable loss of eating quality.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety observed during indexing of plant characteristics with abnormal fungus, bacterial, virus or insect susceptibility is destroyed and eliminated from our breeding program. No atypical resistances/susceptibilities have been noted under normal cultural practices. The present new variety of apricot tree, its flowers foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of apricot tree, substantially as illustrated and described.

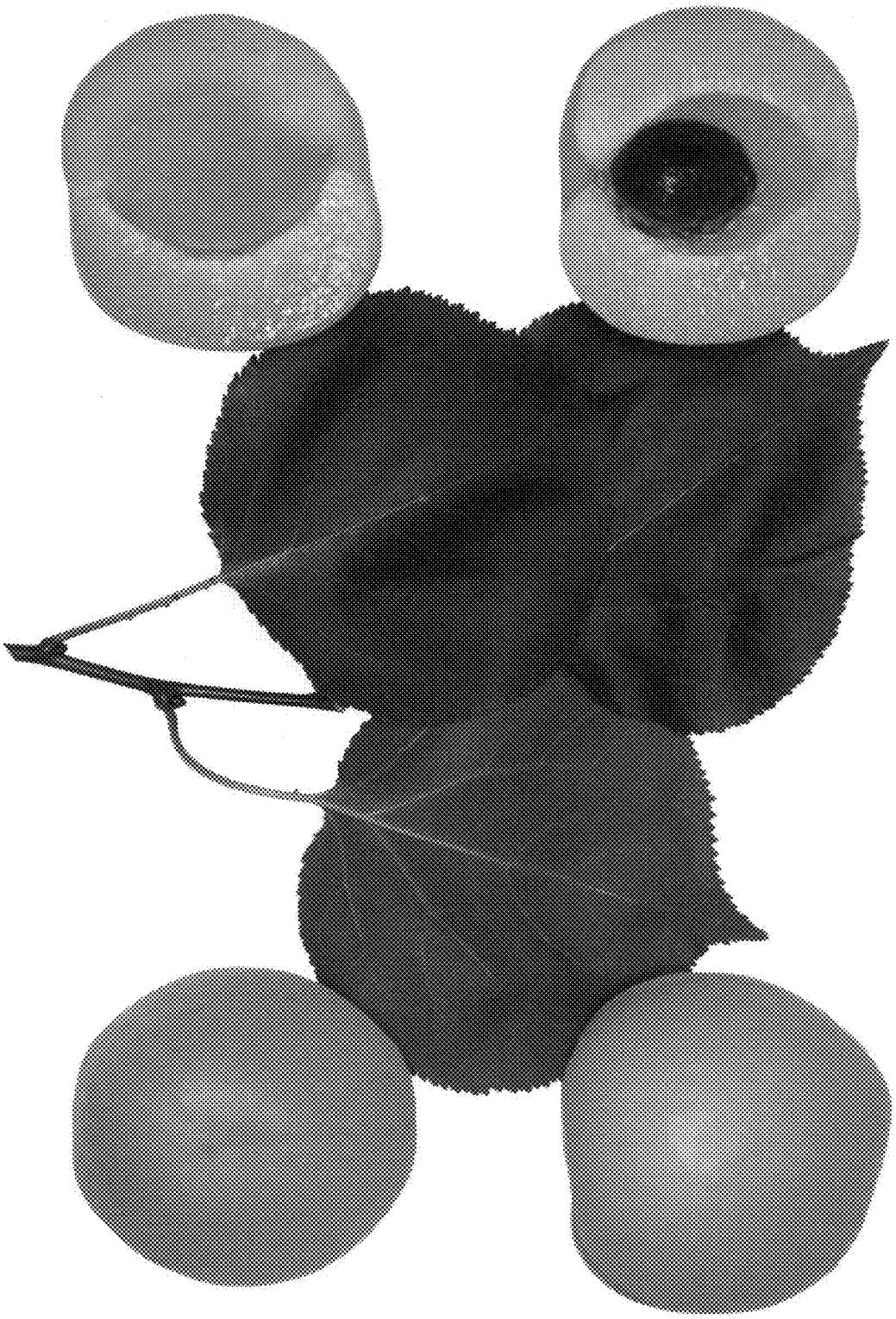

* * * * *